(12) United States Patent
Rickert et al.

(10) Patent No.: US 10,912,209 B2
(45) Date of Patent: *Feb. 2, 2021

(54) MEDICAL IMPLANT AS WELL AS METHOD FOR THE PRODUCTION THEREOF

(71) Applicant: CorTec GmbH, Freiburg (DE)

(72) Inventors: Jörn Rickert, Freiburg (DE); Fabian Kohler, Freiburg (DE); Martin Schüttler, Freiburg (DE)

(73) Assignee: CorTec GmbH, Freiburg (DE)

( * ) Notice: Subject to any disclaimer, the term of this patent is extended or adjusted under 35 U.S.C. 154(b) by 134 days.

This patent is subject to a terminal disclaimer.

(21) Appl. No.: 16/193,788

(22) Filed: Nov. 16, 2018

(65) Prior Publication Data

US 2019/0090366 A1 Mar. 21, 2019

Related U.S. Application Data

(63) Continuation of application No. 14/629,454, filed on Feb. 23, 2015, now Pat. No. 10,251,286, which is a (Continued)

(30) Foreign Application Priority Data

Aug. 24, 2012 (DE) ........................ 10 2012 107 835

(51) Int. Cl.
*H05K 5/02* (2006.01)
*B23K 1/00* (2006.01)
(Continued)

(52) U.S. Cl.
CPC ............. *H05K 5/02* (2013.01); *A61B 5/0031* (2013.01); *A61B 5/686* (2013.01); *B23K 1/0008* (2013.01);
(Continued)

(58) Field of Classification Search
CPC ...... H05K 5/0239; H05K 5/02; H05K 5/0247; H05K 5/0004; A61B 5/0031;
(Continued)

(56) References Cited

U.S. PATENT DOCUMENTS 5,556,421 A 9/1996 Prutchi et al.
2006/0212096 A1* 9/2006 Stevenson ........ G06K 19/07749
607/60

(Continued)

FOREIGN PATENT DOCUMENTS

CN 1907514 A 2/2007
CN 101935208 A 1/2011
(Continued)

OTHER PUBLICATIONS

International Search Report dated Jan. 15, 2014 for corresponding International Application No. PCT/EP2013/067526.
(Continued)

*Primary Examiner* — Christine H Matthews
*Assistant Examiner* — Joshua Daryl D Lannu
(74) *Attorney, Agent, or Firm* — Myers Wolin, LLC

(57) ABSTRACT

Disclosed are a housing for a medical implant, a medical implant for a human or animal organism, a method for manufacturing a medical implant, and a system comprising a medical implant and a transceiver unit that can be coupled to the medical implant.

5 Claims, 6 Drawing Sheets

Related U.S. Application Data continuation of application No. PCT/EP2013/067526, filed on Aug. 23, 2013.

(51) Int. Cl.
  *B23K 1/20* (2006.01)
  *A61B 5/00* (2006.01)
  *H05K 5/00* (2006.01)
  *H04Q 9/14* (2006.01)

(52) U.S. Cl.
  CPC ............... *B23K 1/20* (2013.01); *H04Q 9/14* (2013.01); *H05K 5/0004* (2013.01); *H05K 5/0239* (2013.01); *H05K 5/0247* (2013.01); *A61B 2560/0219* (2013.01); *A61B 2562/029* (2013.01); *A61B 2562/0247* (2013.01); *A61B 2562/0271* (2013.01)

(58) Field of Classification Search
  CPC .... A61B 2562/0247; A61B 2562/0271; A61B 2560/0219; A61B 2562/029; A61B 5/686; B23K 1/20; B23K 1/0008; H04Q 9/14
  See application file for complete search history.

(56) References Cited

U.S. PATENT DOCUMENTS

| | | | |
|---|---|---|---|
| 2006/0217792 A1 | 9/2006 | Hussein et al. | |
| 2007/0167867 A1* | 7/2007 | Wolf | A61B 5/0031 600/561 |
| 2009/0204141 A1* | 8/2009 | Dlugos, Jr. | A61F 5/0059 606/191 |
| 2010/0114205 A1 | 5/2010 | Donofrio et al. | |
| 2010/0114225 A1* | 5/2010 | Imran | A61N 1/36 607/9 |
| 2010/0262208 A1 | 10/2010 | Parker | |

FOREIGN PATENT DOCUMENTS

| | | |
|---|---|---|
| CN | 101939043 A | 1/2011 |
| CN | 102027757 A | 4/2011 |
| DE | 103 23 627 A1 | 12/2004 |
| DE | 10 2011 009 867 A1 | 8/2012 |
| EP | 1184351 A1 | 3/2002 |
| JP | 2010246856 A | 11/2010 |
| JP | 2011500143 A | 1/2011 |
| JP | 2011516198 A | 5/2011 |
| WO | 2009048580 A1 | 4/2009 |
| WO | 2009125903 A1 | 10/2009 |
| WO | 2012126003 A1 | 9/2012 |

OTHER PUBLICATIONS

Chinese Search Report issued for corresponding Chinese Patent Application No. 201380043713X dated Jun. 12, 2016 with an English translation.

German Search Report issued for corresponding German Patent Application No. 10 2012 107 835.1 dated May 2, 2013 with an English translation.

Mi et al., "The Research and Development of Transparent Ceramics", vol. 26, No. 4, Bulletin of the Chinese Ceramic Society, pp. 1, 766-769 and 820, Aug. 2007 with an English translation.

International Preliminary Report on Patentability with the Written Opinion issued for corresponding International Patent Application No. PCT/EP2013/067526 dated Feb. 24, 2015 with an English abstract and an English translation.

Notice of Reasons for Rejection issued for corresponding Japanese Patent Application No. 2015-527929 dated Jul. 3, 2017 with an English Translation.

* cited by examiner

MEDICAL IMPLANT AS WELL AS METHOD FOR THE PRODUCTION THEREOF

CROSS REFERENCE TO RELATED APPLICATIONS

This application is a continuation of U.S. application Ser. No. 14/629,454, filed Feb. 23, 2015, which is a continuation of International Application No. PCT/EP2013/067526, filed Aug. 23, 2013, which claims priority to German Application No. 10 2012 107 835.1, filed Aug. 24, 2012, the contents of each of which are incorporated by reference herein.

FIELD OF THE INVENTION

The invention relates to a medical implant for a human or animal organism, a housing for a medical implant, a method for the production of a medical implant, as well as a system which comprises the medical implant according to the invention, and a transceiver unit which can be coupled to the medical implant.

BACKGROUND OF THE INVENTION AND PRIOR ART

It is known to arrange medical implants, in particular, active medical implants for a human or animal organism in a housing which then is implanted into the human or animal body. The implant housings, thereby, are mostly made from metal shells. Further, it is known to configure the implants such that a communication between the implant and an external transceiver unit is enabled. The communication, hereby, is carried out via radio or inductance.

During communication via inductance, however, the transmission bandwidth is restricted by the carrier frequency. In case the carrier frequency is selected to be high for a high bandwidth, i.e., high data traffic, then it will be attenuated by the materials of the housing and/or by the biological tissue. The thus resulting loss has to be compensated for in that the transmission power is increased accordingly, the latter being detrimental in case the implant is powered by a battery. An increased transmission power may also be detrimental to the biological tissue surrounding the implant if, for example, due to the increased transmission power, the tissue immediately surrounding the implant is heated directly or indirectly by the inherent electrical losses of the electronic circuits.

Further, with respect to the implant housings known from prior art it is disadvantageous that moisture, for example, body fluid enters into the housing which may impair the implant electronics within the housing. It is known to design implants or implant housings such that a leak through which moisture may enter has to be correspondingly small. The expected durability of the implant is estimated during production by measuring the leak. This, however, is disadvantageous in case the implant has to be designed such that it does not have to be replaced during the lifetime of the patient, and has to operate reliably, if needed, over many decades. However, in case moisture enters into the implant housing, functional disorders or even failure of the implant may occur, thus, being detrimental to the patient's health.

Therefore, it is an object of the invention to provide solutions for a medical implant which at least partially overcomes the disadvantages known from prior art, and which enables a high bandwidth of communication between the implant and an external transceiver unit with a high durability of the implant at the same time.

SUMMARY

This object is solved according to the invention by a medical implant for a human or animal organism, a housing for a medical implant, a method for the production of a medical implant, as well as a system which comprises a medical implant, and a transceiver unit which can be coupled to the medical implant, according to the independent claims. Preferred embodiments and further developments of the invention are specified in the respective dependent claims.

Accordingly, a housing for a medical implant is provided wherein a housing wall of the housing is configured to be at least partially transparent, in particular, transparent to infrared light. It is advantageous if the housing wall or at least parts thereof which is/are transparent to light or transparent to infrared light is/are transparent to light having a wavelength of approximately between 700 nm and 1000 nm, preferably between 850 nm and 900 nm. Light of these wavelengths is absorbed at least by the body tissue and, therefore, is suited very well for data transmission.

The information is transmitted in a manner known per se in that the infrared light source is switched on and off in short sequences which is registered by the respective infrared receiver. As protocol, the IrDA may be provided.

Communication is enabled through the light or infrared transparent housing wall between the implant and an external transceiver unit in bidirectional manner by means of infrared radiation. Thereby, a more energy-efficient and interference-free transmission at higher data rates is enabled. Because an infrared transmission unit is integrated into the housing of the medical implant, or may be arranged in the housing and the data transmission results from the light or infrared transparent area of the housing wall, the housing may be designed in a more air-tight or moisture-tight manner because apertures in the housing wall for cables for the communication with the external transceiver unit may be omitted.

The housing, in particular, the area of the housing which is configured to be transparent to light, may comprise ceramics, in particular, aluminum oxide or zirconium oxide in amorphous, crystalline and/or partially crystalline form, a high temperature multi-layer ceramic with an aluminum oxide proportion, or a glass or glass ceramic.

The area of the housing or housing wall which is configured to be transparent to light, may be formed by a cover which covers the opening in the housing wall. In an advantageous embodiment of the invention, the cover may comprise one of the materials mentioned above.

Moreover, a medical implant for a human or animal organism is provided which has a housing with a housing wall which has at least one area configured to be transparent to light, in particular, transparent to infrared light, and comprises an infrared transmission means and/or infrared receiver means arranged in the interior of the housing.

Because the housing wall is configured to be transparent to light or infrared light, a communication may be performed between the implant and an external transceiver unit through a housing wall. The bandwidth of the communication connection, thereby, can be increased substantially. A further advantage is that the handling and the production of a medical implant can be substantially simplified by integration of all components into a housing. Moreover, additional apertures in the housing for the connection of an external communication unit are omitted allowing a more compact system design and increasing the reliability because, for example, mechanical weak points at the housing do not occur. Further, due to the data rates which are realizable by the infrared technology, the application range of the implant is substantially increased, and allows the use of more complex and electronic systems for more complex applications.

It has been found to be advantageous if the area which is configured to be transparent to light comprises ceramics, in particular, aluminum oxide or zirconium oxide in amorphous, crystalline, and/or partially crystalline form, a high temperature multi-layer ceramic having an aluminum oxide proportion, or a glass or a glass ceramics.

It has been found that these materials have sufficient high transparency for infrared rays at different thicknesses between about 150 µm and 2 µm.

In an embodiment of the invention, the area being configured to be transparent to light may be formed by a cover which covers an opening in the housing wall. Thereby, the transparent area of the housing can be created in a particularly simple manner which has different materials than the rest of the housing.

It has been found to be advantageous if at least one sensor, in particular, a moisture sensor, and/or a temperature sensor, and/or a pressure sensor, is arranged in the interior of the housing which is coupled operatively to the infrared transmission means and/or infrared receiver means.

Thereby, the possibility is provided in an advantageous manner to acquire parameters of the surroundings of the electronic circuit which are relevant for the reliable operation, for example, moisture, pressure, or temperature of the housing or of the interior of the housing and to communicate the latter via the infrared interface to the outside.

It is advantageous if at least one magnet, in particular, a permanent magnet is arranged within the interior of the housing which may cooperate with magnets of an external transceiver unit arranged outside of the housing. Thereby, a simple alignment of the external transceiver unit with respect to the medical implant may result.

Advantageously, the energy supply of the implant results from magnetic induction wherein an alternating magnetic field required for wireless transmission of energy is provided outside of the body. The alternating magnetic field is not used for the transmission of data such that the alternating magnetic field does not have to be modulated for the purpose of data transfer, and thereby, the use of induction coils with very high quality is enabled on the transmission side and on the receiver side (implant). Thereby, a very efficient coupling to the sender or to the sender-sided induction coil is enabled.

In a preferred embodiment of the implant, the induction coil may be formed by an electrical conductor wrapped around the implant housing. Hereby, it is advantageous if the implant housing is made from ceramics. By means of the coil, the alternating magnetic field is transformed to voltage in the implant.

By the combination of inductive energy supply of the implant with a (bidirectional) IR data transmission, an energy-saving implementation of the implant is possible because the implant, for example, is only activated upon applying the alternating magnetic field to the implant. Moreover, the implant and, in particular, the data transmission are substantially more insensitive to electromagnetic interferences. Further, an internal energy supply, for example, an accumulator, may be provided within the implant which, if needed, can be charged with the transmitted energy inductively. A further advantage is the separation of (bidirectional) data transmission and energy supply.

It has been found to be of further advantage if a desiccant, for example, getter materials, is provided in the housing interior. Thereby, the moisture within the interior of the housing can be reduced, thus, contributing to the protection of the electronic components arranged within the interior of the housing. The desiccant may be applied to the inner wall of the housing.

In an embodiment of the invention, the area of the housing being configured to be transparent to light may have a lower thickness than the rest of the housing. Thereby, a stable housing may be provided which only has a lower thickness in the area which is configured to be transparent to light for the infrared communication.

Further, it has been found to be advantageous if an electrical shielding, for example, a metal foil, is arranged at the inner wall of the housing wherein the electrical shielding is configured such that it is transparent to light or infrared light at predetermined locations.

Further, it may be advantageous to coat the housing with materials which are transparent to light or infrared light. In an embodiment of the invention, the plastics coating can be provided for mechanical protection and for increase of the biocompatibility of the implant which comprises an area configured to be transparent to light or infrared light. Also, the wrapped induction coil may be coated by the plastics coating. Hereby, a multi-layered plastics coating can be provided. In a further embodiment of the invention the exterior side of the housing may be coated with materials which are favorable for biological processes, for example, tissue repair.

Further, a method for the production of a medical implant, in particular, an implant according to the invention, is provided wherein a. a first substantially frame-shaped metal layer or metallic layer is applied onto a top side of a base substrate, b. an infrared transmission means and/or infrared receiver means is/are arranged on the top side of the base substrate and within the first frame-shaped metallic layer, c. a cover substrate is arranged on the top side of the base substrate which covers the area within the first frame-shaped metallic layer and which has at least one area configured to be transparent to light, in particular, transparent to infrared light wherein a second frame-shaped metallic layer corresponding to the first frame-shaped metallic layer is provided at the cover substrate, and d. the first frame-shaped metallic layer is connected to the second frame-shaped metallic layer non-releasably such that the base substrate, the cover substrate, and the frame-shaped metallic layers together form a substantially hermetically sealed housing of the implant.

Hermetically sealed means that the housing is air-tight, and/or water-tight, or moisture-tight to a large extent or completely such that no malfunctions of the implant due to moisture will occur during the intended operating period which may be several years or decades.

Because the infrared transmission means and/or infrared receiver means is/are arranged in the interior of the housing, the production of an implant may be facilitated substantially because apertures in the housing wall for data communication can be omitted such that during the production of an implant no measures have to be taken in order to close such apertures in an air-tight or water-tight manner.

Between the first frame-shaped metallic layer and the second frame-shaped metallic layer, a circumferential frame, preferably a metal frame, may be arranged wherein the circumferential frame is connected to the two metallic layers non-releasably.

The area configured to be transparent to light can be formed by a cover by means of which an opening in the cover substrate can be closed.

In an embodiment of the invention, the cover substrate may be configured such that the transparent area has a lower thickness than the remaining area of the cover substrate.

It is advantageous if for the transparent area, ceramics, in particular, aluminum oxide or zirconium oxide in amorphous, crystalline and/or partially crystalline form, high temperature multi-layer ceramics with an aluminum oxide proportion, or a glass or glass ceramics is/are used.

At least one sensor, in particular, a moisture sensor, and/or a temperature sensor, and/or the pressure sensor may be arranged within the interior of the housing which is/are coupled operatively to the infrared transmission means and/or infrared receiver means.

Alternatively or additionally, a magnet may be arranged within the interior of the housing, in particular, a permanent magnet which may cooperate with a magnet of an external transceiver unit which can be arranged outside of the housing.

Alternatively or additionally, the housing may be wrapped by an induction coil which is provided as inductive receiver coil for an inductive energy transmission. Preferably, an induction coil having a very high quality is provided for this. It is advantageous if the induction coil is only used for the energy transmission but not for a wireless data transmission.

Further, additionally or alternatively, a desiccant may be arranged within the interior of the housing.

Further, a system is provided by the invention comprising a medical implant for a human or animal organism, in particular, an implant according to the invention, and a transceiver unit wherein the transceiver unit cooperates with an infrared transmission means and/or infrared receiver means of the implant. The transceiver unit may comprise an infrared transmission means and/or an infrared receiver means. The infrared transmission means and/or infrared receiver means of the implant and the infrared transmission means and/or infrared receiver means of the transceiver unit may be coupled operatively through an area of the housing of the implant configured to be transparent to light, in particular, transparent to infrared light.

BRIEF DESCRIPTION OF THE DRAWINGS

Further details and features of the invention as well as concrete embodiments of the invention can be derived from the following description in connection with the drawing in which.

DETAILED DESCRIPTION OF THE PREFERRED EMBODIMENTS

According to the present invention, the communication between a medical implant and a transceiver unit which may be arranged exterior to the body is effected on the basis of light or infrared light wherein the communication can be carried out in a bidirectional manner. In order to enable this, at least a part of the implant housing is configured to be transparent to light or infrared light.

The communication of implants with the outside world, for example, with a transceiver unit arranged outside of the body, is necessary, on the one hand, to check the functionality and the condition of the implant. For this, no high bandwidths or information transmission rates are required.

On the other hand, the communication or transmission of physiological data is necessary for various diagnostic and therapeutic applications. Such data are, for example, blood pressure, temperature, hormone or other messenger material concentrations, or the electrical activity of nerves or muscles. The data transmission on the basis of light or infrared light, hereby, has found to be particularly advantageous because these data can be transmitted with high-performance, i.e., with a high information content, in an energy-saving and secure manner, i.e., with low error/loss rates such that these data are usable for clinical purposes.

Vice versa, also the communication of the outer world, for example, of a transceiver unit arranged outside of the body, with the implant is possible. Thereby, for example, the implant may be switched on or off, or new functional modes can be notified to the implant. For this, no high bandwidths or information transmission rates are necessary.

According to the invention, it is also possible to perform a lasting up to a continuous communication in order to react flexible and fast during therapeutic applications. For example, thereby the supply of substances can be controlled fast and independent of a condition, micro-pumps can be controlled according to the demand, or an electric stimulation of nerves and muscles can be realized fast and according to the demand. For example, the neural stimulation with respect to Parkinson patients according to the demand, or the reactive stimulation with respect to epilepsy patients is possible in case an imminent seizure is measured.

Contrary to a reaction mode determined in the interior of the implant, control from the outside brings along two substantial advantages. A first advantage is that a physician or the patient himself may adapt the activity of the implant at any time. For example, the patient may adapt the effect of the implant by direct control of the exterior transmission unit immediately. A second advantage is that the activity of the implant may be controlled by means of information from the exterior. For example, the activity of an optical prosthesis can be controlled automatically up and down by means of the intensity of light (inside/outside, day/night).

Figure 1:
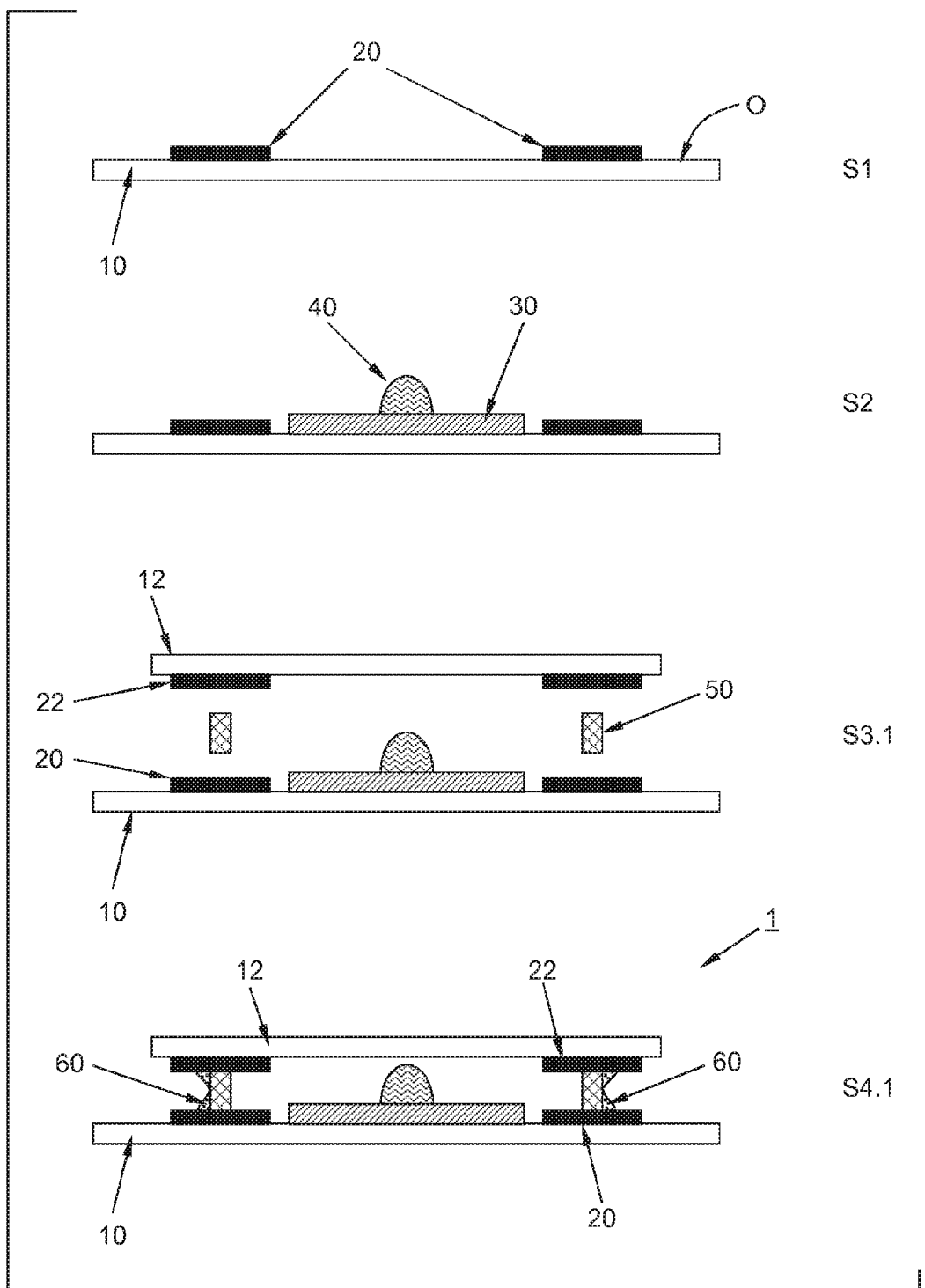
FIG. 1 shows the steps of the production method of a medical implant according to a first embodiment.
Figure 2:
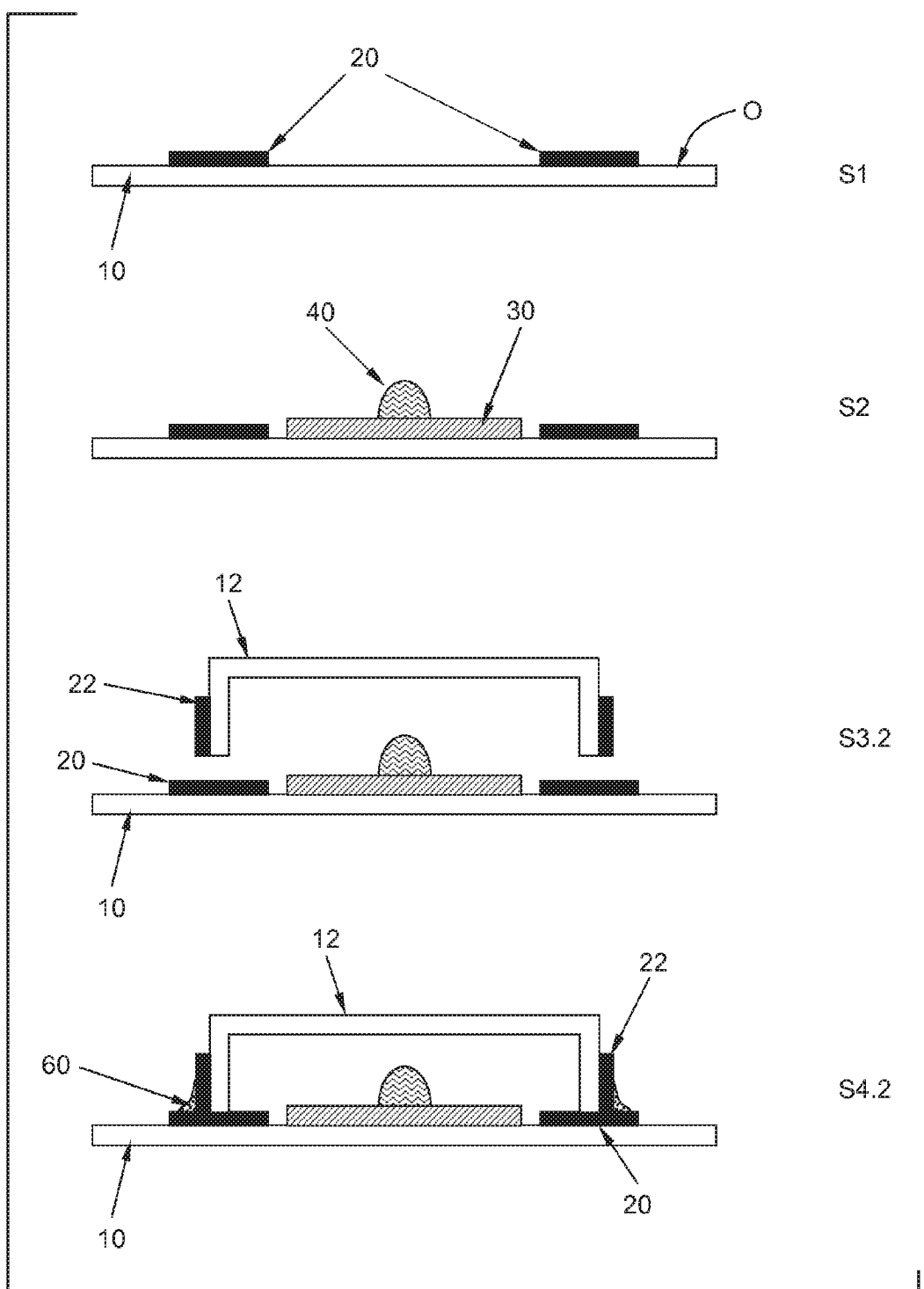
FIG. 2 shows the steps of the production method of an implant according to the invention according to a second embodiment.

FIG. 1 and FIG. 2 show the essential method steps of two methods for the production of the medical implant according to the invention. The first two method steps S1, S2 in the production method according to the first variant (FIG. 1) are identical to the two first method steps S1, S2 of the production method according to a second variant according to the invention (FIG. 2).

In a first step S1, a metallic layer or a metallization layer is applied onto the top side O of the base substrate 10 which basically forms a first frame-shaped metallic layer 20. The first frame-shaped metallic layer 20 serves as solder base for further elements of the housing of the medical implant.

In the subsequent production step S2, all electronic components are arranged on the top side O of the base substrate 10 and within the first frame-shaped metallic layer 20 and are fixed to the base substrate 10. The electronic components, here, comprise the circuit board 30 and an infrared transmission means and/or infrared receiver means 40 arranged on the circuit board 30 wherein the infrared transceiver unit, here, comprises an infrared diode. Further electronic components, for example, sensors, for example, temperature sensors, moisture sensors, or pressure sensors, may be arranged on the circuit board 30, as will be further explained with reference to FIG. 4.

In a third step S3.1 of the production method according to the first variant shown in FIG. 1, a cover substrate 12 is arranged on the top side O of the base substrate 10. The cover substrate 12 covers the area within the first frame-shaped metallic layer 20. At the cover substrate 12 or at the lower side of the cover substrate 12, a second frame-shaped metallic layer 22 is provided which corresponds to the first frame-shaped metallic layer 20 of the base substrate 10. Between the first frame-shaped metallic layer 20 and the second frame-shaped metallic layer 22 additionally a circumferential frame 50 is arranged which basically forms the sidewall of the implant housing. The circumferential frame 50 may be made from a metal.

In a further step S4.1 of the first variant of the production method, the circumferential frame 50 is placed onto the first circumferential metallic layer 20. Subsequently, the cover substrate 12 is placed onto the second circumferential layer 22 such that the second circumferential layer 22 rests on the circumferential frame 50. Subsequently, the circumferential frame 50 is connected to the two metallic layers 20, 22 in a non-releasable manner, resulting, for example, from soldering the two metallic layers 20, 22 to the circumferential frame 50. In FIG. 1, the soldering tin 60 is applied in the area between the two circumferential layers 20, 22.

Thereby, a closed housing system is formed which is substantially air- and moisture-tight, and in the interior of which all electronic components, in particular, the infrared receiver or transmission units are arranged.

The cover substrate 12 is at least partially configured to be transparent to light or infrared light in order to allow for a communication by means of infrared radiation through the housing using an external transceiver unit. Possible embodiments of an area of a housing wall which is transparent to light or infrared light will be explained in further detail with respect to FIG. 5 and FIG. 6.

FIG. 2 shows a second variant of the production method according to the invention of a medical implant according to the invention wherein the production steps S1 and S2 are identical to the production method shown in FIG. 1.

In a third step S3.2 of the second variant of the production method shown in FIG. 2, a cover substrate 12 which here is configured as a half-shell is arranged at the top side of the base substrate 12 such that the rim of the half-shell rests on the circumferential metallic layer 20 of the base substrate 10. The circumferential metallic layer 22 is provided at the external sidewall of the half shell 12 which extends up to the rim of the half shell and thereby comes into contact with the circumferential metallic layer 20 during placing the half shell on the base substrate 12.

In of fourth step S4.2 of the second production variant, the first frame-shaped metallic layer 20 is connected to the second frame-shaped metallic layer 22 non-releasably, for example, by means of a solder method. The soldering tin 60 can be seen in FIG. 2. The cover substrate 12 or the half shell is configured to be transparent to light or infrared light in an area as will be further described with reference to FIG. 5 and FIG. 6.

In order to configure the cover substrate to be transparent to light or infrared light, different materials may be used for the area of the cover substrate which is transparent to light or infrared light. For example, different ceramics may be used with different thicknesses as substrate material for the cover substrate. Examples of such ceramics are, for example, aluminum oxide Al2O3 in amorphous form (Rubalit), in crystalline form (sapphire), or in semi-crystalline form. Alternatively, also glass and glass ceramics can be used. Further, also zirconium oxide ZrO2 or high temperature multi-layer ceramics (HTCC) with a varying proportion of aluminum oxide Al2O3 can be used for the production of the areas which are transparent to light or infrared light.

By adapting the thickness or strength of the substrate material in the area which is transparent to light or infrared light, the infrared transmission, i.e., the transparency for infrared radiation, can be varied.

With respect to the production methods shown with respect to FIG. 1 and FIG. 2, also a production step not shown here may be provided according to which the housing is wrapped by an electrical conductor which forms an induction coil for inductive energy transmission.

Figure 3:
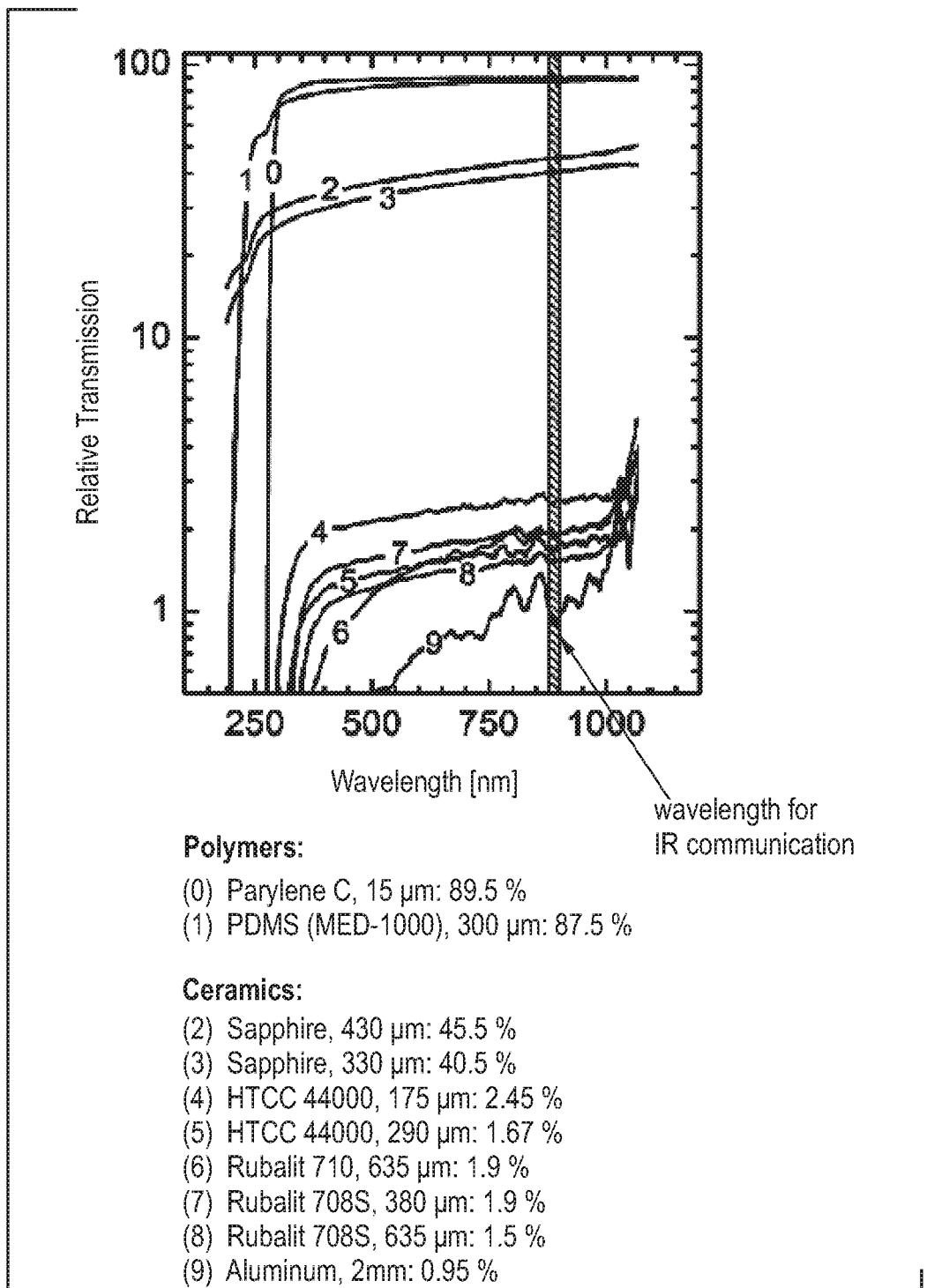
FIG. 3 shows a diagram from which the relative transmission of infrared radiation with respect to the wavelength of the infrared rays and the materials used can be derived.

FIG. 3 shows the relative transmission of infrared light through various materials depending on the wavelength of the infrared light and on the material used wherein the specifications of the relative transmission with respect to the single materials are referred to a wavelength of the infrared radiation between 850 nm and 900 nm.

In the diagram shown in FIG. 3, the relative transmission for Rubalit, sapphire, and a high temperature multi-layer ceramic (HTCC) is shown for respectively different thicknesses. Further, in the diagram of FIG. 3, also the relative transmission for aluminum with a thickness of 2 mm, for Parylene C with a thickness of 15 μm, and for polydimethylsiloxane PDMS (MED-1000) with a thickness of 300 μm is plotted.

As can be seen from FIG. 3, the infrared transparency can be increased in that the respective material is made thinner. Further, the materials are the more transparent to infrared radiation the more crystalline the material is, as is also visible in FIG. 3.

For air- or moisture-tight encapsulation of the housing, materials which can be soldered, for example, copper, or copper foil are suitable. Also possible are hermetic housings from titanium or stainless steel wherein in these housings, an area transparent to light or infrared light has to be provided (for example, sapphire, ruby, diamond, or a similar solid crystal or gemstone which is transparent to light or infrared light, or similar ceramics which are transparent to light or infrared light) has to be provided, as shown, for example, with reference to FIG. 5.

As soldering tin for non-releasable connection of the cover to the bottom of the housing, all conventional alloys can be used wherein however, lead-free materials are preferable.

Further, it may be necessary to cast the housing in a medical elastomer or to coat the housing with a medical elastomer. For this, conventional medical silicones may be used, for example, polydimethylsiloxane. Alternatively or additionally, the housing can be coated or encapsulated for this by a polymer, for example, Parylene C.

The infrared transmission properties are influenced by the polydimethylsiloxane as well as by Parylene C only insignificantly, as can be seen from FIG. 3.

Figure 4:
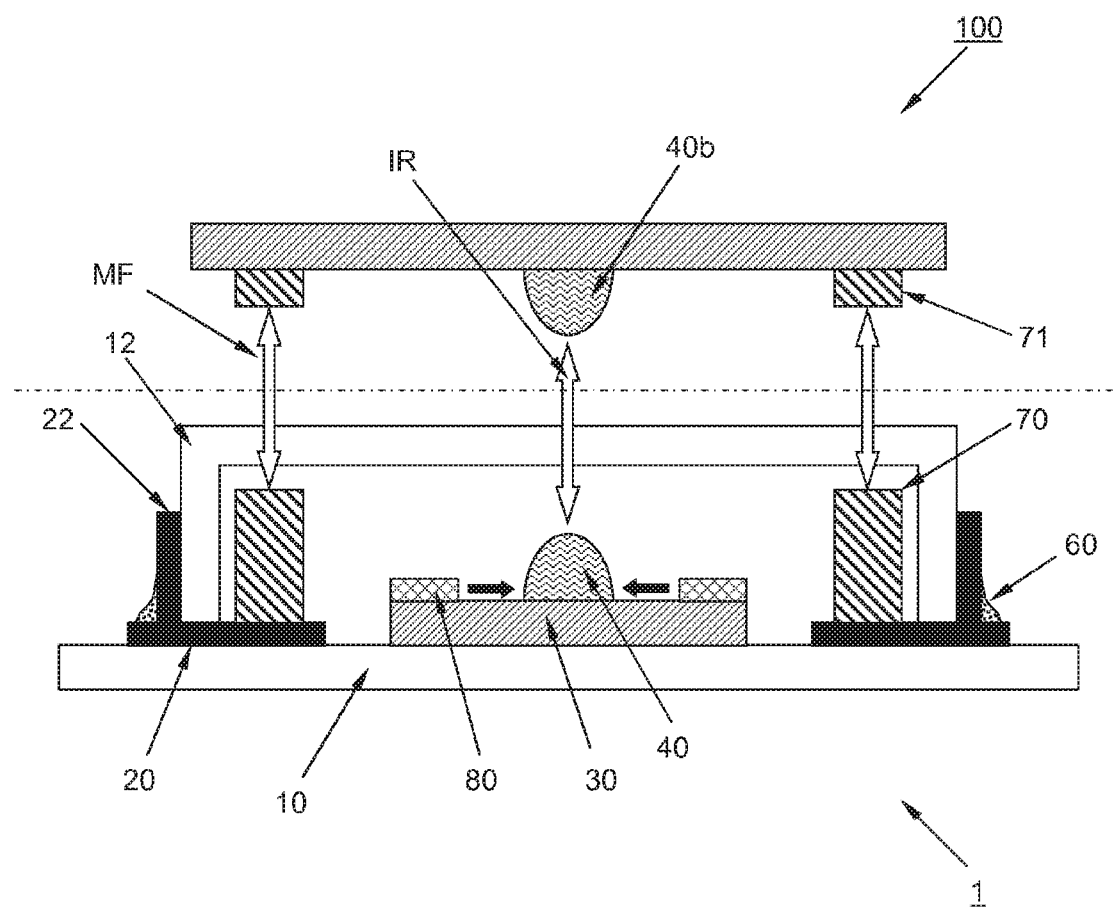
FIG. 4 shows a schematic assembly of a medical implant according to the invention.

FIG. 4 shows a system according to the invention which comprises a medical implant 1 and an external transceiver unit 100. The communication between the implant 1 and the external transceiver unit 100 is effected on the basis of infrared radiation. The cover substrate 12 of the implant 1 is configured to be at least partially transparent to light or infrared light for this such that an infrared data transmission IR between the implant 1 and the external transceiver unit 100 is possible.

The implant 1 shown in FIG. 4 has been produced according to the production method shown in FIG. 2. Prior to closing the housing in steps S3.2 or S4.2, magnets 70 have been arranged in the interior of the housing which are configured as permanent magnets. The external transceiver unit 100 which comprises an infrared transmitter and/or infrared receiver 40b also has magnets or permanent magnets 71 which correspond to the magnets 70 of the implant 1. Thereby, an alignment of the external transceiver unit 100 with respect to the implanted implant 1 can be supported. Also shown in FIG. 4 is the magnetic field MF formed between the respective magnets.

Further, prior to closing the housing, a number of sensors 80 can be arranged in the interior of the housing in steps S3.2 or S4.2. For example, a moisture sensor, a temperature sensor and/or a pressure sensor may be provided. The sensors are coupled to the infrared transceiver means 40 of the implant 1 such that the sensor values of the sensors can be transmitted by means of IR communication to the external transceiver unit 100.

The magnet 70 and the sensors 80 may also be arranged in the interior of the housing in the steps S3.1 and S4.1 according to the production method shown in FIG. 1.

The moisture in the interior of the implant housing can be checked in regular intervals by means of a moisture sensor which preferably has a very low drift. In case the sensor value of the moisture sensor exceeds a critical value, this can be indicated to the user such that a replacement of the implant due to safety reasons is suggested to the user. Thereby, it is possible to leave the implant in the body of the patient as long as possible. The merely prophylactic replacement of an implant, thus, can be prevented.

For the extension of time in which the moisture within the implant housing is very low and thereby allows for a reliable operation of the electronic components arranged within the housing interior, desiccants can be introduced into the housing which bind the water entering into the interior of the housing up to a certain amount chemically or physically such that they cannot contribute to an increase of the air moisture within the interior of the housing. For this, so called getter materials can be provided. The desiccant or the getter material may be applied onto the housing wall wherein the infrared transmission is effected through the substrate material and the desiccant or the getter material.

The temperature sensor may be provided in order to further increase the reliability of the electronics within the housing. The temperature sensor may, for example, be used in order to prevent a thermal overload of the implant or a not intended heating of the tissue surrounding the implant. In case the temperature exceeds a predetermined value, counter measures can be initiated by the implant. For example, the functioning of the implant can be reduced to a minimum function. The measured temperature values can be transmitted also by means of IR communication to the external transceiver unit 100. Upon frequent exceeding of certain temperature values, a replacement of the implant may be proposed to the patient or to the user.

Figure 5:
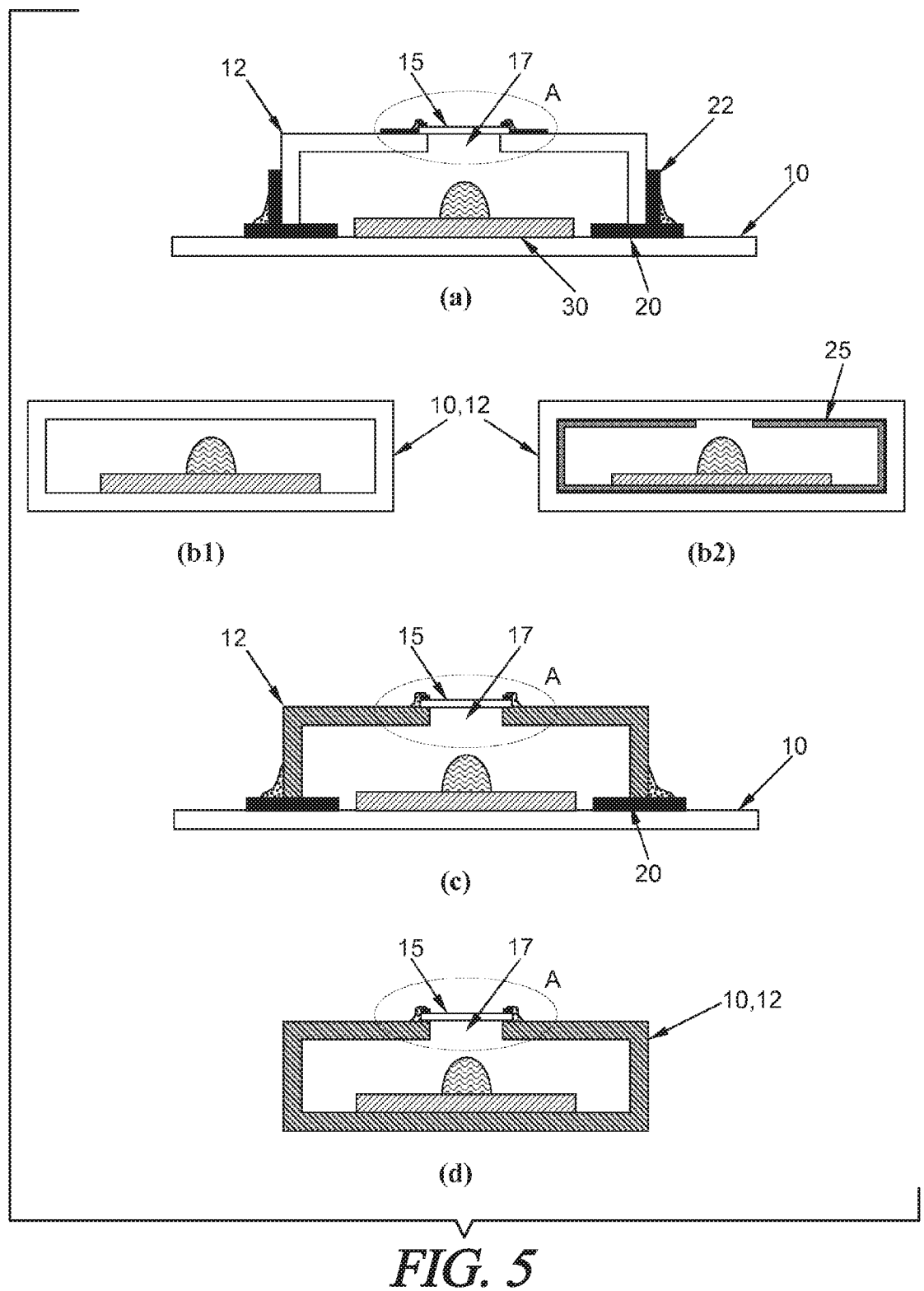
FIG. 5 shows five different design variants of a medical implant according to the invention.

FIG. 5 shows five variants of a medical implant for a human or animal organism according to the invention.

With respect to the variants in (a), (c), and (d), the cover substrate 12 has an opening 17 which is closed by a cover 15 wherein the cover 15 is configured to be transparent to light or infrared light. As materials for the cover 15, the materials mentioned above can be used. The cover substrate 12 does not have to be configured to be transparent to light or infrared light in these embodiments.

The cover 15 is soldered onto the cover substrate 12 wherein a metallic layer is applied onto the cover substrate 12 and in the rim-sided region of the cover 15 depending on the material used for the cover substrate 12 in order to allow a soldering of the cover substrate 12 to the cover 15. In the variant (a), corresponding metallic layers are applied to the cover substrate 12 as well as to the cover 15. With respect to the variant (c), corresponding metallic layers are only applied on the cover 15 because according to this variant, the cover substrate is configured metallically. Also, according to the variant (d), a corresponding metallic layer is also only provided on the cover 15.

With respect to the variant (d), the cover substrate 12 as well as the base substrate 10 is metallic.

According to variant (b1), the housing is made as one piece wherein the entire housing 10, 12 comprises a material transparent to light or infrared light.

The variant (b2) differs from the variant according to (b1) in that an electrical shielding is applied to the inner walls of the housing, for example, a metal foil wherein the shielding comprises an area which is transparent to light or infrared light. The area of the shielding 25 which is transparent to light or infrared light may be realized by a recess in the metal foil.

Figure 6:
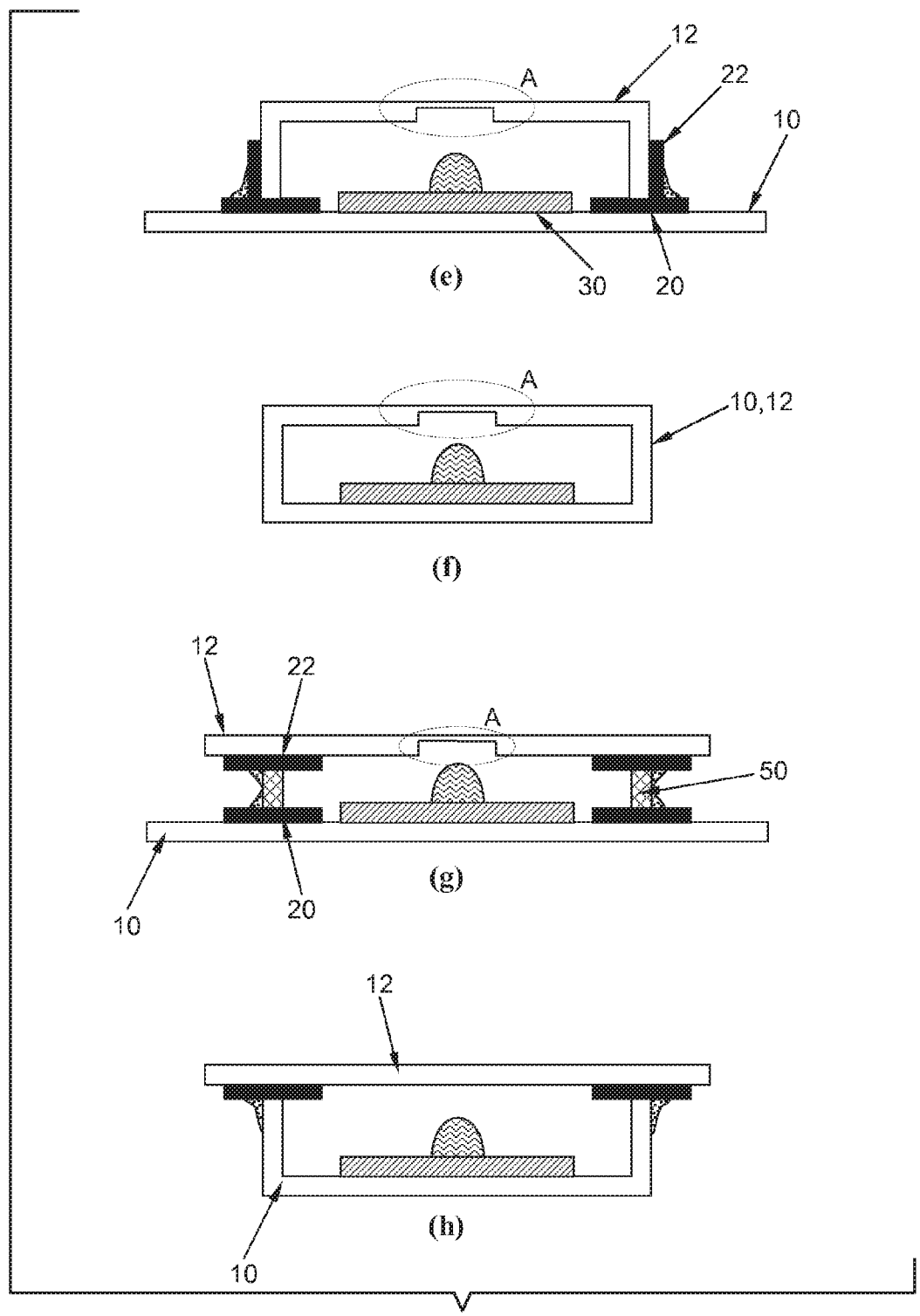
FIG. 6 shows four further design variants of a medical implant according to the present invention.

The metallic shielding shown in the variant (b2) may be provided for all variants shown in FIG. 5 and FIG. 6.

FIG. 6 shows four further variants of a medical implant according to the invention.

With respect to the variants (e), (f), and (g), the cover substrate 12 is made thinner in the area in which the cover substrate is to be configured transparent to light or infrared light than in the remaining area of the cover substrate. The thickness or strength of the area of the cover substrate which is transparent to light or infrared light may be selected depending on the selected substrate material, as shown with respect to the diagram in FIG. 3.

With respect to the variant (h), the electronic components or the infrared transceiver means 40 of the implant are not arranged on the base substrate 10 but rather on the interior bottom of a cover substrate 12 which is half-shell shaped. In this case, the base substrate 10 has to be configured to be transparent to light or infrared light at the corresponding locations, as shown with reference to the variants (a) to (g) of FIG. 5 and FIG. 6.

REFERENCE NUMERALS 1 medical implant
10 substrate (base substrate) as part of the housing
12 substrate (cover substrate) as part of the housing
15 cover for an opening in the housing wall
17 opening in the housing wall (aperture)
20 first frame-shaped metallic layer on the base substrate
22 second frame-shaped metallic layer on the cover substrate
25 electric current shielding, for example, metal foil 30 circuit board (electronic circuit board)
40 infrared transmission means and/or infrared receiver means of the implant
40b infrared transmission means and/or infrared receiver means of the external transceiver unit
50 circumferential frame, preferably metal frame, as part of the housing
60 non-releasable connection between the first and second frame-shaped metallic layers or between the frame-shaped metallic layers and the metal frame, preferably, soldering tin
70 magnet or permanent magnet in the implant
71 magnet or permanent magnet at the external infrared transceiver unit
80 sensor, for example, moisture sensor and/or temperature sensor and/or pressure sensor
100 external IR transceiver unit
A portion of the housing wall in which the area being transparent to light is located
HTCC high temperature multi-layer ceramics (High Temperature Cofired Ceramics)
IR infrared data transmission
MF magnetic field
O top side of the base substrate
S1 first step of the production method
S2 second step of the production method
S3.1 third step of the production method according to a first variant
S3.2 third step of the production method according to a second variant
S4.1 fourth step of the production method according to a first variant
S4.2 fourth step of the production method according to a second variant

What is claimed is:

1. A method for producing a medical implant for a human or animal organism, the medical implant comprising:
   a housing having a housing wall that has at least one region configured to be permeable to infrared light and an infrared transmitting device or infrared receiving device arranged in an interior of the housing and permitting communication between the implant and an external transmitting/receiving device,
   wherein said at least one region configured to be permeable to infrared light has
      aluminum oxide, $Al_2O_3$, in an amorphous or semi-crystalline form, or zirconium oxide, $ZrO_2$, in an amorphous or semi-crystalline form, or
      high-temperature multilayer ceramic with some aluminum oxide content, and
   with the at least one region of the housing that is configured to be permeable to infrared light having a smaller thickness than a remaining region of the housing, said method comprising:
   on an upper surface of a base substrate of the implant, a first circumferential frame-shaped metallic layer is applied;
   on said upper surface of said base substrate and within said first circumferential frame-shaped metallic layer, the infrared transmitting device or the infrared receiving device is arranged;
   on said upper surface of said base substrate, a cover substrate is arranged which covers a region within said first circumferential frame-shaped metallic layer and which has a least one region configured to be permeable to infrared light, a second circumferential frame-shaped metallic layer coinciding with said first circumferential frame-shaped metallic layer being provided on the cover substrate; and
   said first circumferential frame-shaped metallic layer is undetachably connected to said second circumferential frame-shaped metallic layer in such a manner that the base substrate, the cover substrate and the circumferential frame-shaped metallic layers cooperate to form an essentially hermetically sealed housing of the implant.

2. The method as claimed in claim 1, wherein a circumferential frame is arranged between said first circumferential frame-shaped metallic layer and said second circumferential frame-shaped metallic layer, said frame being undetachably connected to both said first and second circumferential frame-shaped metallic layers.

3. The method as claimed in claim 1, wherein said at least one the region configured to be permeable to infrared light of said housing wall is formed by a lid by means of which an opening provided in the cover substrate is sealed.

4. The method as claimed in claim 1, wherein the cover substrate is configured in such a manner that said at least one region configured to be permeable to infrared light of said housing wall has a smaller thickness than a remaining region of the cover substrate.

5. The method as claimed in claim 1, wherein the at least one region configured to be permeable to infrared light of said housing wall is made with:
   aluminium oxide, $Al_2O_3$, in an amorphous or semi-crystalline form, or zirconium oxide, $ZrO_2$, in an amorphous or semi-crystalline form, or
   high-temperature multilayer ceramic with some aluminium oxide content.

* * * * *